United States Patent
Nguyen et al.

(10) Patent No.: US 9,892,361 B2
(45) Date of Patent: Feb. 13, 2018

(54) METHOD AND SYSTEM FOR CROSS-DOMAIN SYNTHESIS OF MEDICAL IMAGES USING CONTEXTUAL DEEP NETWORK

(71) Applicant: SIEMENS HEALTHCARE GMBH, Erlangen (DE)

(72) Inventors: Hien Nguyen, Bensalem, PA (US); Shaohua Kevin Zhou, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 136 days.

(21) Appl. No.: 15/003,119

(22) Filed: Jan. 21, 2016

(65) Prior Publication Data
US 2016/0210749 A1    Jul. 21, 2016

Related U.S. Application Data

(60) Provisional application No. 62/105,854, filed on Jan. 21, 2015.

(51) Int. Cl.
| | |
|---|---|
| *G06N 3/08* | (2006.01) |
| *G06T 11/00* | (2006.01) |
| *G06N 3/04* | (2006.01) |
| *G06F 19/00* | (2011.01) |
| *A61B 5/00* | (2006.01) |

(52) U.S. Cl.
CPC .............. *G06N 3/084* (2013.01); *A61B 5/00* (2013.01); *G06N 3/0454* (2013.01); *G06T 11/00* (2013.01); *A61B 5/0035* (2013.01); *G06F 19/30* (2013.01)

(58) Field of Classification Search
None
See application file for complete search history.

(56) References Cited

U.S. PATENT DOCUMENTS

| | | | |
|---|---|---|---|
| 2015/0170002 A1* | 6/2015 | Szegedy | G06K 9/4628 382/156 |
| 2015/0238148 A1* | 8/2015 | Georgescu | A61B 5/7267 600/408 |
| 2016/0174902 A1* | 6/2016 | Georgescu | G06T 7/73 600/408 |
| 2016/0239706 A1* | 8/2016 | Dijkman | G06F 17/3028 |

(Continued)

OTHER PUBLICATIONS

Lee et al. "Identifying Multiple Abdominal Organs From CT Image Series Using a Multimodule Contextual Neural Network and Spatial Fuzzy Rules," IEEE Transactions on Information Technology in Biomedicine, vol. 7, No. 3, Sep. 2003.*

(Continued)

*Primary Examiner* — Matthew Bella
*Assistant Examiner* — Soo Shin (57) ABSTRACT

A method and apparatus for cross-domain medical image synthesis is disclosed. A source domain medical image is received. A synthesized target domain medical image is generated using a trained contextual deep network (CtDN) to predict intensities of voxels of the target domain medical image based on intensities and contextual information of voxels in the source domain medical image. The contextual deep network is a multi-layer network in which hidden nodes of at least one layer of the contextual deep network are modeled as products of intensity responses and contextual response.

23 Claims, 7 Drawing Sheets

(56) References Cited

U.S. PATENT DOCUMENTS

2016/0300351 A1* 10/2016 Gazit .................. G06T 7/11
2017/0076438 A1* 3/2017 Kottenstette ....... G06K 9/00637

OTHER PUBLICATIONS

Zhao et al. "Predictive Encoding of Contextual Relationships for Perceptual Interference, Interpolation, and Prediction," Proc. Int. Conf. Learn. Represent., Dec. 24, 2014.*

* cited by examiner

METHOD AND SYSTEM FOR CROSS-DOMAIN SYNTHESIS OF MEDICAL IMAGES USING CONTEXTUAL DEEP NETWORK

This application claims the benefit of U.S. Provisional Application No. 62/105,854, filed Jan. 21, 2015, the disclosure of which is herein incorporated by reference.

BACKGROUND OF THE INVENTION

The present invention relates to synthesis of medical image data, and more particularly, to synthesizing medical image data across image domains or image modalities.

A multitude of imaging modalities, such as computed tomography (CT), diffuser tensor imaging (DTI), T1-weighted magnetic resonance imaging (MRI), T2-weighted MRI, ultrasound, X-ray, positron emission tomography (PET), etc., can be used for medical image analysis of a of a patient. Each of these imaging modalities captures different characteristics of the underlying anatomy and the relationship between any two modalities is highly nonlinear. These different imaging techniques provide physicians with varied tools and information for making accurate diagnoses. However, sensor heterogeneity creates challenges for developing effective automatic image analysis platforms. In particular, algorithms that work well on one modality can be rendered useless on data collected from a different type of scanner.

In many practical medical image analysis problems, a situation is often encountered in which medical image data available for training, for example for machine learning based anatomical object detection, has a different distribution or representation than the medical image data given during testing due to modality heterogeneity or domain variation. Due to variations in the image characteristics across modalities, medical image analyses algorithms trained with data from one modality may not work well when applied to medical image data from a different modality. One way to address this issue is to collect large amounts of training data from each imaging modality. However, this solution is impractical since collecting medical images is often time consuming and expensive.

Cross-modal synthesis generates medical images in a desired target modality from given source modality images. The ability to synthesize medical images without actual acquisition has many potential applications, such as atlas construction, virtual enhancement, multi-modal registration, and segmentation. Various approaches for cross-modal synthesis have been proposed, but such approaches are typically tailored to specific applications or based on various heuristics.

BRIEF SUMMARY OF THE INVENTION

The present invention provides a method and system for cross-domain synthesis of medical images. Embodiments of the present invention utilize a novel deep network architecture called a contextual deep network (CtDN) in order to synthesize a medical image in a target domain or modality from a medical image in a source domain or modality. Hidden nodes of the CtDN are models as products of feature responses and contextual responses, which enables the CtDN to capture dependencies of target voxels' intensities on both source voxel's intensities and spatial locations. Embodiments of the present invention can be used with any pair of imaging modalities.

In one embodiment of the present invention, a source domain medical image is received. A synthesized target domain medical image is generated using a trained contextual deep network (CtDN) to predict intensities of voxels of the target domain medical image based on intensities and contextual information of voxels in the source domain medical image. The contextual deep network is a multi-layer network in which hidden nodes of at least one layer of the contextual deep network are modeled as products of intensity responses and contextual response.

These and other advantages of the invention will be apparent to those of ordinary skill in the art by reference to the following detailed description and the accompanying drawings.

DETAILED DESCRIPTION

The present invention relates to a method and system for cross-domain synthesis of medical images using a contextual deep network. Embodiments of the present invention are described herein to give a visual understanding of the medical image synthesis method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide a generalized and robust framework for cross-modality or cross-domain synthesis of medical images. Embodiments of the present invention can be used to synthesize medical images in a target domain from available images in a source domain without having to perform image acquisition in the target domain. Embodiments of the present invention may be used to synthesize target domain medical images in order to create large training set of target domain medical images for training machine learning based classifiers for anatomical object detection, segmentation, tracking, and classification, without having to perform additional image acquisition on a large number of subjects. In addition, embodiments of the present invention may be used to synthesize target domain medical images for other applications, such as to create visualization tools for virtual domains, to perform cross-modality registration, to up-sample the resolution of image data, or for image segmentation. As used herein, cross-domain synthesis refers to synthesis of medical images across medical imaging modalities, such as synthesizing a CT image from an MR image, as well as synthesis of images across an image domain, such MR images with different protocols (e.g., T1 and T2), contrast CT images and non-contrast CT images, CT image captured with low kV and CT images captured with high kV, or any type of low resolution medical image to a corresponding high resolution medical image. That is, the "source domain" and "target domain" may be completely different medical imaging modalities or different image domains or protocols within the same overall imaging modality.

Figure 1:
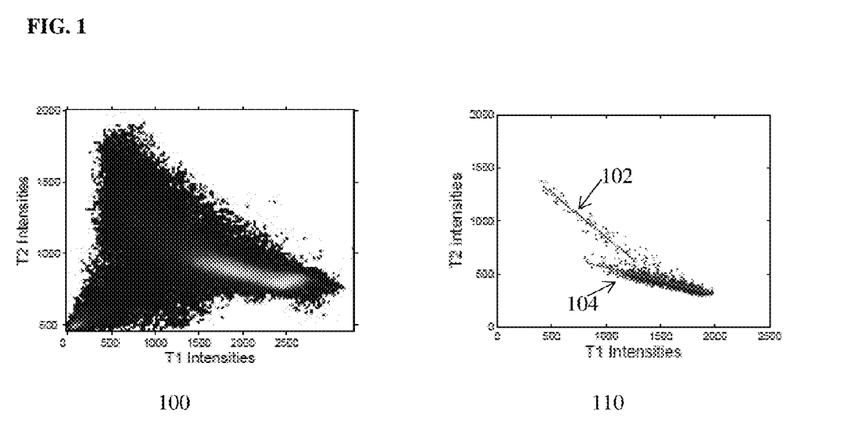
FIG. 1 illustrates intensity correspondences between T1 and T2 magnetic resonance imaging (MRI) scans of the same subject.

Deep or layered compositional architectures are able to model complex functions, and by adding extra hidden layers to a deep model, its representational power strictly improves. Recently, deep architectures have led to several important breakthroughs in computer vision and speech processing. As deep architectures include desirable properties such as the ability to model complex mappings and fast run-times, the present inventors have addresses the challenges of cross-domain synthesis using a deep network. However, the present inventors have determined that a vanilla multilayered network that uses only intensity features does not perform well enough for cross-domain medical image synthesis. In order to better understand the reason why such a vanilla multilayered network is not effective one can observe correspondences between intensities in a source domain image and a target domain image. FIG. 1 illustrates intensity correspondences between T1 and T2 magnetic resonance imaging (MRI) scans of the same subject. Image (a) of FIG. 1 shows a plot of intensity correspondences between the T1 and T2 scans over the entire images. It can be observed in image (a) that the intensity transformation between the T1 scan and the T2 scan is not only non-linear, but also far from unique. That is, there are multiple feasible intensity values in the MRI-T2 domain for one intensity vale in the MRI-T1 domain. The non-uniqueness results from the fact that the intensity values depend on the anatomical regions in which the voxels reside. As a result, learning a vanilla deep network for predicting MRI-T2 intensity values from MRI-T1 intensity values may not be particularly effective. Image (b) shows intensity correspondences between the T1 and T2 scans within a restricted local neighborhood of 10×10×10 voxels in the images. In can be observed in image (b) that the intensity variation is much simpler within the local neighborhood. The correspondence in the local neighborhood could reasonably be described as a union of two linear subspaces represented by lines 102 and 104. That is to say, the present inventors have determined that the spatial information helps to simplify the relations between modalities which in turn can enable more accurate prediction of the intensities of the voxels in the target modality. Accordingly, embodiments of the present invention provide technique in which spatial constraints can be encoded into a deep network.

Figure 2:
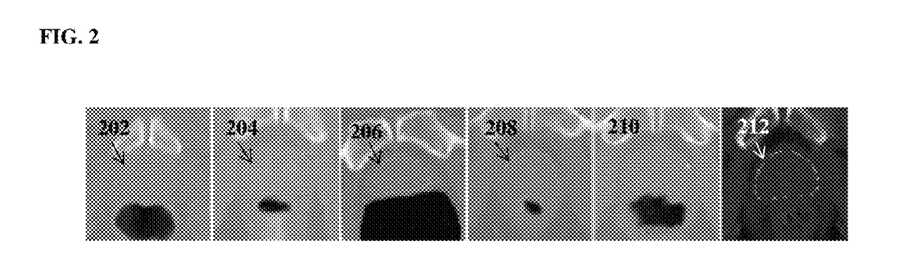
FIG. 2 illustrates exemplary CT prostate images used for cross-domain synthesis based segmentation.

FIG. 2 illustrates exemplary CT prostate images used by the present inventors for cross-domain synthesis based segmentation experiments. In such cross-domain synthesis based segmentation, the CT prostate images are the source domain images and segmentation mask images showing a segmented prostate are the target domain images. The prostate boundaries 202, 204, 206, 208, 210, and 212 are shown in the CT images of FIG. 2. It can be observed that it is extremely difficult to visually distinguish between prostate regions inside the prostate boundaries 202, 204, 206, 208, and 210 and their surroundings in the CT images. This is due to the low contrast of CT images. As a result, a vanilla deep network using intensity features would not be able to accurately predict the segmentation masks. The present inventors have determined that it is beneficial to use additional contextual information, such as voxels' positions with respect to pelvic bones, to help the cross-domain synthesis used to generate the prostate segmentation masks from the CT prostate images. Embodiments of the present invention effectively integrate both context and intensity features into a deep architecture in order to perform such cross-domain image synthesis.

In contrast to traditional deep network architectures, embodiments of the present invention model responses of hidden nodes as the product of feature responses and contextual responses. As a result, the same input feature can give rise to different outputs depending on the context. In an advantageous embodiment, with an appropriate response function and contextual variables such as voxels' spatial locations, spatial locality constraints are incorporated into the deep network architecture. The ability to capture joint distribution of feature and spatial variables is advantageous in achieving high-quality synthesis. Embodiments of the present invention can be applied to any source and target modalities or domains. Embodiments of the present invention are also computationally efficient since most computations are simple feed-forward filtering operations. In contrast, other image synthesis approaches, which use nearest neighbor or sparse coding synthesis, are very computationally intensive.

Figure 3:
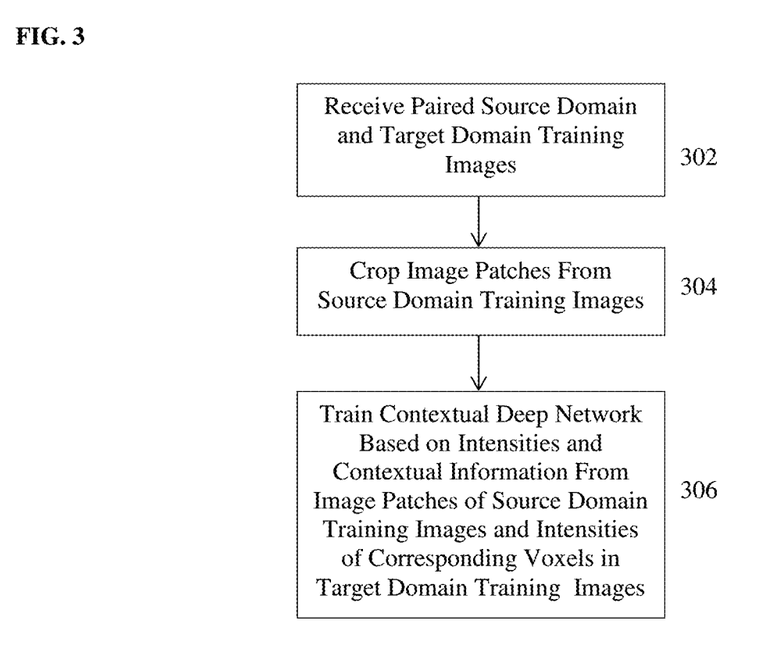
FIG. 3 illustrates a method of training a Contextual Deep Network (CtDN) for synthesizing a target domain image from a source domain image according to an embodiment of the present invention.

FIG. 3 illustrates a method of training a Contextual Deep Network (CtDN) for synthesizing a target domain image from a source domain image according to an embodiment of the present invention. The method of FIG. 3 can be used to train a CtDN for any type of cross-domain or cross-modality medical image synthesis, including but not limited to, synthesizing an MR image of one type of MR protocol (e.g., T2 MR image) from an MR image of another type of MR protocol (e.g., T1 MR image), synthesizing a contrast CT image from a non-contrast CT image, synthesizing a high-kV CT image from a low-kV CT image, synthesizing a high resolution medical image from a low resolution medical image of the same modality, synthesizing a segmented image mask from an input medical image for image segmentation, synthesizing a CT image from an MR image, or for any other combination of imaging modalities (e.g. MR, CT, PET, DynaCT, etc.).

At step 302, paired source target domain training images and target domain target images are received. The source domain training images will also be referred to herein as the "source training images" and the target domain medical images will also be referred to herein as the "target training images". The source training images and target training images are paired, such that for every source training image in the source domain there is a corresponding target training image of the same subject in the target domain. The source and target training images can be acquired using any type of medical imaging modality, such as MR, CT, Ultrasound, X-ray fluoroscopy, DynaCT, positron emission tomography (PET), etc. In an exemplary embodiment, the source training images can be one type of MR image (e.g., MRI-T1) and the corresponding target training images can be another type of MR image (e.g., MRI-T2). In another exemplary embodiment, in which the CtDT is trained for image synthesis based segmentation, the source training images can be medical images of a particular modality and the corresponding target training images can be segmentation masks resulting from segmenting a particular anatomical structure in the source training images. In the description provided herein it is assumed that the source and target training images are 3D medical images, but the present invention is not limited thereto and the source and target images can be 2D or 3D medical images. It is to be understood that although the source and target training images can be 2D or 3D, we use the term "voxel" herein to refer to elements of these images, regardless of the dimensionality of the medical image. In an exemplary implementation, the source and target training images can be a previously acquired medical images in the source and target domains, respectively, that have been paired and are stored in a database on a memory or storage of a computer system, or stored remotely on a server or other network device, and the source and target training images are received by loading the paired source and target training images to a computer system performing the method of FIG. 3.

At step 304, image patches are cropped from the source training images. The source training images are cropped image patches of size l×l×l. For example, in a possible implementation l can be equal to 3, such that the source training images can be cropped into 3×3×3 image patches. Intensity values and contextual information are extracted from each of the image patches of the source training images and used as input for training the CtDN. In an advantageous embodiment, the spatial location of each image patch in the source training image from which it was cropped is used as the contextual information. In this case, for each image patch of the source training images, the voxel intensities $s_n$ of the voxels in the source image patch and the coordinates $x_n$ of the center voxel of the source image patch, denoted as $(s_n, x_n)$, are stored and used as input for training the CtDN. For each image patch of a source training image, the intensity value $t_n$ of the voxel in the paired target training image corresponding to the center voxel in the source image patch (i.e., having the same coordinates in the target training image as $x_n$) is stored and associated with that source image patch as the target output.

At step 306, the CtDN is trained based on the intensities and contextual information from the image patches of the source training images and the intensities of the corresponding voxels in the target training images. Deep networks are machine learning based networks that learn a relationship between input data and output data with multiple hidden layers of learned features or variables between the input data and the output data. According to an advantageous aspect of the present invention, a contextual deep network (CtDN) is deep or multi-layer network in which the nodes of at least one hidden layer are modeled as products of feature responses and contextual responses.

Let K denote the number of layers in the network architecture and k denote the index of a specific layer. let $\Psi: \mathbb{R}^s \rightarrow \mathbb{R}^t$ denote the mapping function corresponding to a fully connected network, where s is the input dimension and t is the output dimension. $\{s_n, t_n\}_{n=1}^N$ represents input training samples and their corresponding output, respectively. $F^k$, $h^k$, $b^k$ are the set of filters, hidden nodes, and biases, respectively, at the k-th layer of the network. $p_k$ is the number of hidden units of the k-th layer. $x_n$ and $\hat{x}_i$ represent contextual information of the input and i-th hidden unit respectively. We use the notation "∘" to indicate the Hadamard product between vectors or matrices. $\|.\|$ denotes the $l_2$-norm of a vector. All vectors and matrices are denoted in bold letters. Capital letters are used for matrices and lower-case letters are used for vectors. sigm(.) Represents the sigmoid function.

First, the training of a fully connected deep network will be described and then the training of the CtDN will be described. In the embodiments described herein, the mean square-error loss function is used for training the fully connected deep network and the CtDN. However, the present invention is not limited to the mean square-error loss function and other loss functions, such as soft-max, cross-entropy, and hinge loss can also be used. Using the mean square-error loss function, the function to be optimized to train a vanilla fully connected deep network (without contextual information) takes the following form:

$$E = \frac{1}{2N} \sum_{n=1}^{N} \|\psi(s_n) - t_n\|^2 \quad (1)$$

Figure 4:
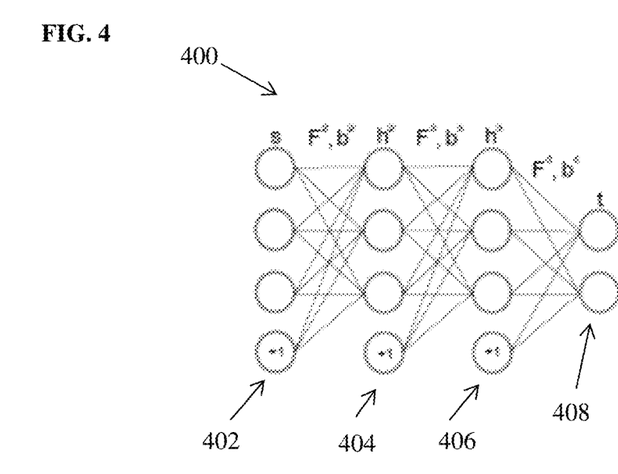
FIG. 4 illustrates an exemplary fully connected multi-layer network.

Here, $\Psi(.)$ is a mapping that is carried out by a multi-layer network. FIG. 4 illustrates an exemplary fully connected multi-layer network 400. As shown in FIG. 4, the multi-layer network 400 includes four layers 402, 404, 406, and 412. The first layer 402 is equivalent to the input vector s and the last layer 410 predicts the output values t.

The learning of the network's parameters can be performed using the well-known back propagation algorithm. Since the error over the entire training dataset is calculated as a sum of the individual errors, it is sufficient to describe backpropagation for a single sample, say the n-th sample. For the simplicity of notation, the subscript "n" will be omitted. The filtering operation and response of the hidden nodes at each layer of the network is computed as:

$$u^k = F^k h^{k-1} + b^k \quad (2)$$

$$h^k = \gamma(u^k) \quad (3)$$

Here, $\gamma(.)$ is a non-linear rectification function, such as the sigmoid or tanh function, that is applied element-wise on a vector. Note there are no hidden units in the first layer and $h^1$ (e.g., layer 402 in FIG. 4) is considered to be the same as input vector s. For image synthesis, the vanilla deep network is trained directly on the image intensity data and the input vector s is a vector of voxel intensities for a training sample.

At the heart of the backpropagation algorithm is a recursive computations of the derivative of E with respect to the parameters $(F^k, b^k)$ at each layer. In particular, the term that propagates backward through the network is the same as the "sensitivities" of each hidden node to the perturbations of its bias, as expressed in Equation (4):

$$d^k = \frac{\partial E}{\partial u^k} = \frac{\partial E}{\partial b^k} \quad (4)$$

The second equality in Equation (4) is because the partial derivative of $u^k$ with respect to $b^k$ is an all-one vector. For efficient computation, the training algorithm first performs a forward pass to compute the output activations $h^k$, followed by a backward pass to generate deltas $d^k$ for each layer. The partial derivative $d^k$ propagates from a higher layer to the adjacent lower layer through the following relationship:

$$d^k = (F^{k+1})^T d^{k+1} \circ \gamma'(u^k) \quad (5)$$

This relationship can be easily verified using the chain rule. Note that the above expression in Equation (5) only applies for intermediate layers, i.e., $k \in [2, K-1]$ (e.g., layers 404 and 406 of FIG. 4). The sensitivity of the first layer, which takes a slightly different form, is computed as follows:

$$d^K = (\Psi(s) - t) \circ \gamma'(u^K) \quad (6)$$

The gradient for updating the filters' weights is calculated as a product of the hidden nodes' responses from the previous layer and the sensitivities of the current layer:

$$\frac{\partial E}{\partial F^k} = d^k h^{k-1^T} \quad (7)$$

The whole network can be efficiently trained using the stochastic gradient descent algorithm with the gradients given in Equations (4) and (7). The learning rate or step size in the gradient descent algorithm is an important parameter is training a deep network. In an advantageous implementation, a larger learning rate can be used at the beginning of the training and then the learning rate can be gradually decreased towards the end of the training.

While the vanilla deep network describe above is trained using only input features (e.g., voxel intensities of the training images), in an advantageous embodiment of the present invention, the CtDN is trained using feature responses (e.g., voxel intensities) and contextual information (e.g., spatial locations) extracted from the training data. The CtDN models multiplicative interactions between input features and contextual information. This multiplicative interaction is useful for enforcing spatial locality constraints in the input-output mapping. The CtDN is augmented with contextual variables x which convey a different type of information not present in s. In the CtDN, the responses of hidden nodes of at least one layer of the multi-layer network are modeled as the product of the feature response and the contextual response. In an advantageous embodiment, the responses of the hidden nodes in the second layer are computed as the product of feature response and contextual response, as expressed in Equation (8):

$$h^2 = \gamma(u^2) \circ \zeta(x; \theta) \quad (8)$$

Figure 5:
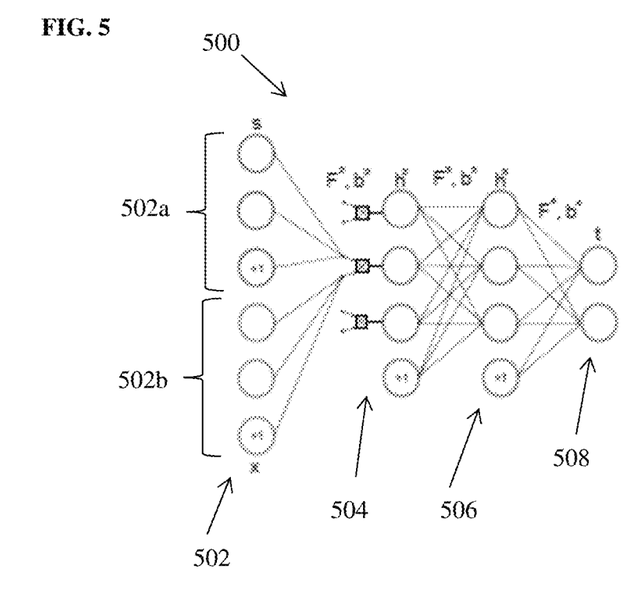
FIG. 5 illustrates an exemplary contextual deep network (CtDN) according to an embodiment of the present invention.

Here, $\zeta(.; \theta)$ is a non-linear function that maps an input contextual vector x to the unit interval [0,1]. This function serves as a switch that turns hidden units on in certain contexts and off in others. FIG. 5 illustrates an exemplary contextual deep network (CtDN) 500 according to an embodiment of the present invention. As shown in FIG. 5, the CtDN 500 includes four layers 502, 504, 506, and 508. The first layer 502 is equivalent to the input vectors s and x. Nodes 502*a* represent the input feature variables s and nodes 502*b* represent the contextual variables x. The second layer 504 of the CtDN 500 uses product nodes to model the responses of the hidden nodes of the second layer 504 as products of the feature responses and the contextual responses. For better clarity, connections are only shown between the input layer 502 and one product node. The product nodes multiply the hidden nodes' responses to the input features ($\gamma(u^2)$) and the responses to the contextual variables ($\zeta(x; \theta)$), as expressed in Equation (8). Accordingly, when $\zeta(x; \theta)$ maps the input contextual vector to zero, this product is equal to zero and the hidden node is "switched off". When $\zeta(x; \theta)$ maps the input contextual vector to one, the product is equal to the feature response $\gamma(u^2)$, and the hidden node is "switched on". In an alternative implementation, it is also possible that the contextual vector can be mapped to a value between zero and one such that the produce of the feature response and the contextual response weights the feature response of the hidden unit based on the contextual information. The choice of the contextual variables and the function $\zeta$ may be dictated by the specific application at hand. Possible options for x include anatomical labels, Cartesian coordinates of voxels, and relative coordinates of voxels with respect to some landmarks.

In order to apply the backpropagation algorithm to train the CtDN, the present inventors have derived the gradient of the error E with respect to $(F^2, b^2, \theta)$. Using the chain rule, the present inventors have derived the partial derivative for the second layer as:

$$d^2 = \frac{\partial E}{\partial b^2} = \frac{\partial E}{\partial u^2} = \left(\frac{\partial u^3}{\partial h^2}\right)^T \frac{\partial E}{\partial u^3} \circ \frac{\partial h^2}{\partial u^2} \quad (9)$$

$$= F^3 d^3 \circ \gamma'(u^2) \circ \zeta(x; \theta) \quad (10)$$

The expression in Equation (10) is similar to the expression in Equation (5), but includes a modification in which each dimension of the gradient is scaled by the corresponding element of $\zeta(x; \theta)$. Similarly, the partial derivative of E with respect to $F^2$, which is the same as in Equation (7), can be computed as:

$$\frac{\partial E}{\partial F^2} = \frac{\partial E}{\partial u^2}\left(\frac{\partial u^2}{\partial F^2}\right)^T = d^2 h^{1^T} = d^2 s^T \quad (11)$$

This expression remains correct when extended to the case of multiple training samples in which $d^2$ and $h^1$ are matrices. Finally, the derivative of E with respect to $\theta$ can be expressed as:

$$\frac{\partial E}{\partial \theta} = \left(\frac{\partial u^3}{\partial h^2}\right)^T \frac{\partial E}{\partial u^3} \circ \frac{\partial h^2}{\partial \theta} = F^{3^T} d^3 \circ \gamma(u^2) \circ \frac{\partial \zeta(x; \theta)}{\partial \theta} \quad (12)$$

This gradient depends on the form of the function $\zeta(x; \theta)$, which is application-specific. The training is performed jointly for all parameters using the back-propagation algorithm with the modified gradients of the second layer provided in Equations (10), (11), and (12).

According to an advantageous embodiment of the present invention, spatial locations are used as the context information for training the CtDN to synthesize images of one domain from images captured in another domain. This allows the CtDN to effectively model the mapping between the source domain and the target domain since the CtDN can take into account both intensity features and special cues. In an advantageous implementation, the Cartesian coordinates of voxels in the source training images as used as contextual variables. This implicitly conveys anatomical information relating to the voxels. In this case, $\zeta(.; \theta)$ can be implemented as:

$$\zeta(x; \theta) = 2 \times sigm\left(-\left[\frac{\|x - \hat{x}_1\|^2}{\sigma^2}, \ldots, \frac{\|x - \hat{x}_{p_2}\|^2}{\sigma^2}\right]^T\right) \quad (13)$$

Hence, the function $\zeta(.; \theta)$ maps the input x vector to a vector whose elements are in [0,1]. As previously defined, $p_2$ is the number of hidden units (nodes) in the second layer and $\hat{x}_i$ is the augmented variables associated with the i-th hidden node in the second layer. With this function $\zeta$, the parameters $\theta$ can be expressed as $\theta = (\sigma, \hat{X})$, where $\hat{X} = [\hat{x}_1, \ldots, \hat{x}_{p_2}]$ are learned and $\sigma$ is constant. In an exemplary implementation $\sigma$ can be equal to 0.5, but the present invention is not limited thereto. In the present inventors' experiments, all dimensions of the vector x are divided by 100. Using the relationship expressed in Equation (12), the partial derivative of the error with respect to $\hat{x}_i$ can be derived as:

$$\frac{\partial E}{\partial \hat{x}_i} = [F^{3T} \cdot d^3 \circ \gamma(u^2) \circ \tau]_i \times (\hat{x}_i - x) \quad (14)$$

$$\tau = 2\varsigma(x; \theta)(1 - \varsigma(x; \theta)) \quad (15)$$

where $[.]_i$ indicates the i-th element of a vector. Using this partial derivative, along with the partial derivatives expressed in Equations (10) and (11) to optimize the second layer of the network, which uses the contextual information, the whole network can be optimized using the gradient descent algorithm, as described above for the vanilla fully connected network. The training is done jointly for all parameters using the back-propagation algorithm, with the modified gradients expressed in Equations (10), (11) and (14)-(15).

Figure 6:
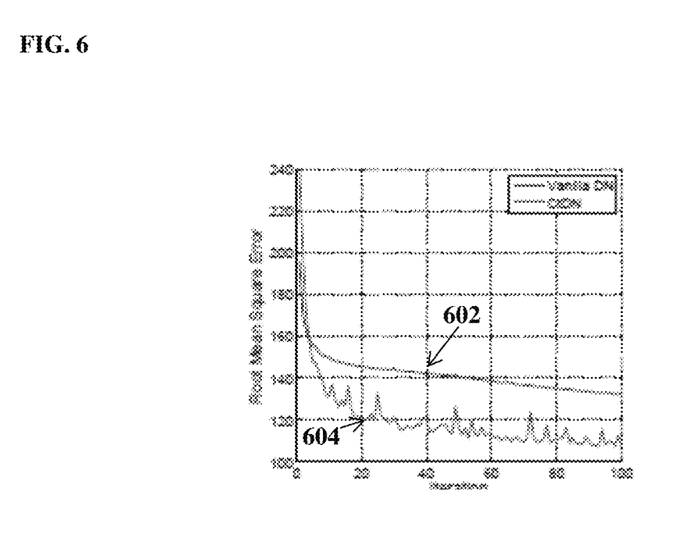
FIG. 6 illustrates a comparison of training error of the CtDN with that of a vanilla deep network.

FIG. 6 illustrates a comparison of training error of the CtDN with that of the vanilla deep network. FIG. 6 shows the training error over 100 training epochs of a vanilla deep network 602 and the CtDN 604, each have which were trained to synthesize MRI-T2 images from MRI-T1 images. The vanilla deep network was trained to predict MRI-T2 intensity values from MRI-T1 intensity values. The CtDN was trained to predict MRI-T2 intensity values from MRI-T1 intensity values in which spatial coordinates of voxels serve as the contextual information. As shown in FIG. 6, the training error of the CtDN 604 goes significantly lower than the training error of the vanilla deep network 602, even though both networks were trained with the same parameters for the learning rate and the number of hidden nodes.

Figure 7:
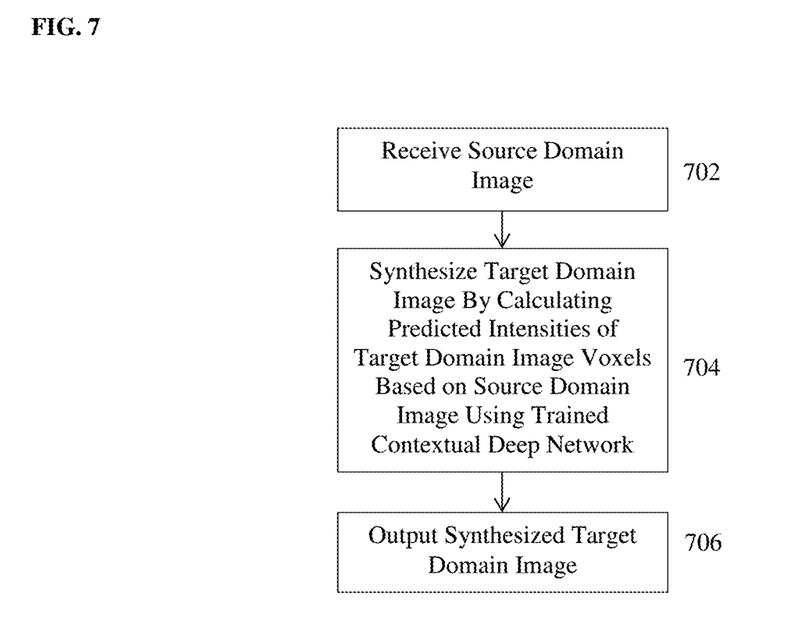
FIG. 7 illustrates a method for synthesizing a target domain medical image from a source domain medical image according to an embodiment of the present invention.

FIG. 7 illustrates a method for synthesizing a target domain medical image from a source domain medical image according to an embodiment of the present invention. The method of FIG. 7 transforms medical image data of a first domain or modality (source domain) to generate a new medical image of a second domain or modality (target domain). The method of FIG. 7 uses a trained CtDN in order to synthesize a new target domain image from a received source domain image. The CtDN can be trained (using the method of FIG. 5) in an offline training phase and stored on a storage or memory of a computer system or stored remotely on a server or cloud based system. The method of FIG. 7 can be used for any type of cross-modal modality medical image synthesis, including but not limited to, synthesizing an MR image of one type of MR protocol (e.g., T2 MR image) from an MR image of another type of MR protocol (e.g., T1 MR image), synthesizing a contrast CT image from a non-contrast CT image, synthesizing a high-kV CT image from a low-kV CT image, synthesizing a high resolution medical image from a low resolution medical image of the same modality, synthesizing a segmented image mask from an input medical image for image segmentation, synthesizing a CT image from an MR image, or for any other combination of imaging modalities (e.g. MR, CT, PET, DynaCT, etc.).

At step 702, a source domain medical image is received. The source domain medical image will also be referred to herein as the "source image". The source image can be acquired using any type of imaging modality, such as MR, CT, Ultrasound, X-ray fluoroscopy, DynaCT, positron emission tomography (PET), etc. The medical image can be a 2D or 3D medical image. It is to be understood that although the medical image can be 2D or 3D, we use the term "voxel" herein to refer to elements of the medical image, regardless of the dimensionality of the medical image. In one possible implementation, the source image can be a previously acquired medical image that is stored on a memory or storage of a computer system, or stored remotely on a server or other network device, and the source image is received by loading the source image to a computer system performing the method of FIG. 7. In another possible implementation, the source image can be received directly from an image acquisition device, such as an MR scanner, CT scanner, etc.

At step 704, a target domain medical image is synthesized by predicting voxel intensities of the target domain medical image based on the source domain medical image using a trained contextual deep network (CtDN). The target domain medical image will also be referred to herein as the "target image". The trained CtDN is a multi-layer network in which the hidden nodes in at least one of the layers are modeled as products of feature responses and contextual responses. The trained CtDN can be trained using the method of FIG. 5 described above. In an advantageous embodiment, the response of the hidden nodes of the second layer of the CtDN are calculated as products of the feature response and the contextual responses. According to an advantageous implementation, the CtDN can predict the intensities of the voxels of the target image based on intensities and spatial locations of voxels in the source image. The trained CtDN can be applied over all of the voxels of the received source image using a sliding window approach. The window defines a current image patch of the source image and voxel intensities and spatial coordinates are extracted from the image patch. For example, a 3×3×3 image patch of the source image can be used, but the present invention is not limited thereto. Voxel intensities of the voxels in the image patch and the spatial coordinates of the center voxel of the image patch are extracted from the current image patch and input to the trained CtDN. The trained CtDN predicts an intensity value for a voxel of the target image corresponding to the current image patch of the source image. The corresponding voxel of the target image is the voxel having the same spatial coordinates in the target image as the coordinates of the center voxel of the current image patch in the source image. The intensity value predicted by the CtDN based on the intensities and spatial coordinates extracted from the current image patch is assigned to the corresponding voxel in the target image. The window is then moved to define a next image patch and the CtDN predicts an intensity value for the voxel in the target image corresponding to the next image patch. This process is repeated for image patches centered at each voxel in the source image so that CtDN predicts, for each voxel in the source image, an intensity value for a corresponding voxel in the target image.

At step 706, the synthesized target domain medical image is output. For example, the synthesized target domain medical image can be displayed on a display of a computer system and/or stored in a storage or memory of a computer system.

The methods of FIGS. 3 and 7 can be used to synthesize medical images across medical imaging modalities, as well as synthesis of images across an image domain. In an exemplary implementation, the present inventors have utilized the methods of FIGS. 3 and 7 to synthesize patient-specific T2-MRI brain images from T1-MRI brain images and vice versa. In the experiments for synthesizing T2-MRI brain images from T1-MRI brain images and synthesizing T1-MRI brain images from T2-MRI brain images, the training source and target images and the input source images were linearly registered, skull stripped, inhomogeneity corrected, histogram matched within each modality, and resampled to 2 mm resolution. The present inventors tested the image synthesis method with two different size settings for the CtDN, denotes as CtDN-1 and CtDN-2. The parameter settings used in these experiments are summarized in Table 1, below:

TABLE 1

| | Parameter | | | |
|---|---|---|---|---|
| | $\{pk\}_{k=1}^{4}$ | $\lambda$ | $\sigma$ | l |
| Value | CtDN-1: [27, 200, 20, 1] | 0.25 | 0.5 | 3 |
| | CtDN-2: [27, 400, 40, 1] | | | |

The present inventors also evaluated the following methods as a basis for comparison: (1) Vanilla deep network—the present inventors used a vanilla deep network with the same size as the CtDN to learn a regression model for predicting the target intensities from the source voxels' intensities; and (2) Modality propagation—this is a general purpose data-driven approach for cross-domain image synthesis, which is a generalization of label propagation to continuous outputs. Since the present inventors have access a database containing both T1-weighted and T2-weighted MR scans for a number of subjects, the synthesized images can be directly compared to ground truth target modality images for evaluation of the synthesis method. The present inventors utilized normalized cross-correlation as the evaluation metric. The present inventors found that CtDN consistently outperforms the vanilla deep network for both T1-T2 and T2-T1 synthesis tasks. The results also indicated the increasing the network size helps to improve the correlation between the synthesized image and the ground truth, at the cost of higher run-time computation.

Figure 8:
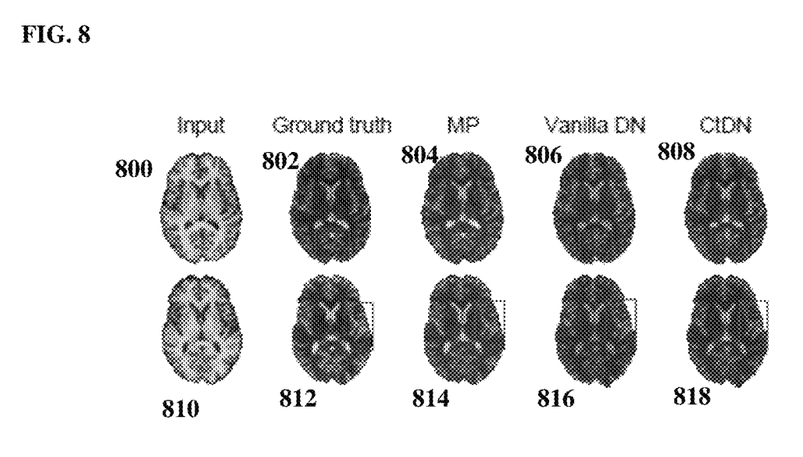
FIG. 8 illustrates exemplary results for synthesizing MRI-T1 images from MRI-T2 images using different approaches.

FIG. 8 illustrates exemplary results for synthesizing MRI-T1 images from MRI-T2 images using the different approaches. Image 800 shows a first input MRI-T2 image and image 802 shows the corresponding ground truth MRI-T1 image. Images 804, 806, and 808 show the synthesized MRI-T1 images generated from the input MRI-T2 image 800 using modality propagation, the vanilla deep network, and the CtDN, respectively. Image 810 shows a second input MRI-T2 image and image 812 shows the corresponding ground truth MRI-T1 image. Images 814, 816, and 818 show the synthesized MRI-T1 images generated from the input MRI-T2 image 810 using modality propagation, the vanilla deep network, and the CtDN, respectively.

In another exemplary implementation, the present inventors have applied the methods of FIGS. 3 and 7 for image synthesis method using a CtDN to prostate segmentation in CT images. The dataset used included 246 CT volumes cropped around the prostate regions. All volumes were resampled to 1 mm resolution. 100 volumes were used for training and the rest for testing. In training, more voxels were sampled around the boundaries of the prostates since those voxels contain more information. Approximately 20 million voxels were used as input for training the CtDN. The parameter settings these experiments on the prostate dataset are summarized in Table 2, below:

TABLE 2

| Parameter | Description | Value |
|---|---|---|
| $\{pk\}_{k=1}^{4}$ | Network size | [343, 400, 40, 1] |
| $\lambda$ | Learning rate | 0.25 |
| $\sigma$ | Constant in $\zeta$ | 0.5 |
| l | Voxel size | 7 |

The Cartesian coordinates of the voxels' centers are used to provide contextual information to the CtDN. The CtDN performed well in synthesizing a segmentation mask that provided a prostate segmentation result.

Figure 9:
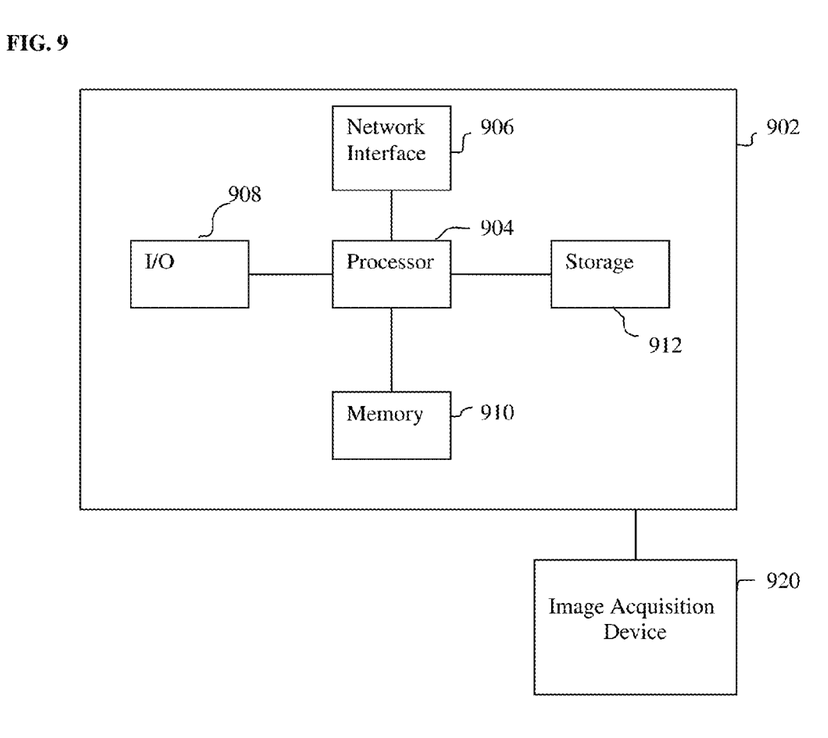
FIG. 9 is a high-level block diagram of a computer capable of implementing the present invention.

The above-described methods for training a contextual deep network and for synthesizing a target domain medical image from a source domain medical image may be implemented on a computer using well-known computer processors, memory units, storage devices, computer software, and other components. A high-level block diagram of such a computer is illustrated in FIG. 9. Computer 902 contains a processor 904, which controls the overall operation of the computer 902 by executing computer program instructions which define such operation. The computer program instructions may be stored in a storage device 912 (e.g., magnetic disk) and loaded into memory 910 when execution of the computer program instructions is desired. Thus, the steps of the methods of FIGS. 3 and 7 may be defined by the computer program instructions stored in the memory 910 and/or storage 912 and controlled by the processor 904 executing the computer program instructions. An image acquisition device 920, such as an MR scanning device or a CT scanning device, can be connected to the computer 902 to input image data to the computer 902. It is possible to implement the image acquisition device 920 and the computer 902 as one device. It is also possible that the image acquisition device 920 and the computer 902 communicate wirelessly through a network. In a possible embodiment, the computer 902 can be located remotely with respect to the image acquisition device 920 and the method steps described herein can be performed as part of a server or cloud based service. In this case, the method steps may be performed on a single computer or distributed between multiple networked computers. The computer 902 also includes one or more network interfaces 906 for communicating with other devices via a network. The computer 902 also includes other input/output devices 908 that enable user interaction with the computer 902 (e.g., display, keyboard, mouse, speakers, buttons, etc.). Such input/output devices 908 may be used in conjunction with a set of computer programs as an annotation tool to annotate volumes received from the image acquisition device 920. One skilled in the art will recognize that an implementation of an actual computer could contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for synthesizing a target domain medical image from a source domain medical image, comprising:
receiving the source domain medical image; and
generating a synthesized target domain medical image using a trained contextual deep network to predict intensities of voxels of the target domain medical image based on intensities and contextual information of voxels in the source domain medical image,
wherein the contextual deep network is a multi-layer network in which hidden nodes of at least one layer of the contextual deep network are modeled as products of intensity responses and contextual response, a response of each hidden node of the at least one layer of the contextual deep network is calculated as a product of a first function of the intensities of the voxels in the source domain medical image and a second function of the contextual information of the voxels in the source domain medical image, and the second function maps the contextual information of the voxels in the source domain medical image to a value of zero or one for each hidden node of the at least one layer of the contextual deep network.

2. The method of claim 1, wherein the contextual information of the voxels in the source domain medical image is spatial locations of the voxels in the source domain medical image.

3. The method of claim 2, wherein generating the synthesized target domain medical image using the trained contextual deep network to predict the intensities of the voxels of the target domain medical image based on the intensities and the contextual information of the voxels in the source domain medical image comprises:
for each of a plurality of image patches in the source domain medical image,
extracting intensities of voxels in the image patch and spatial coordinates of a center voxel in the image patch; and
calculating an intensity of a corresponding voxel in the target domain medical image based on the intensities of the voxels in the image patch of the source domain medical image and the spatial coordinates of the center voxel in the image patch of the source domain medical image using the trained contextual deep network, wherein the corresponding voxel in the target domain medical image is a voxel having the same spatial coordinates in the target domain medical image as the center voxel in the image patch of the source domain medical image.

4. The method of claim 1, wherein the at least one layer of the contextual deep network comprises a second layer of the contextual deep network.

5. The method of claim 4, wherein the contextual information of the voxels in the source domain medical image is spatial coordinates of the voxels in the source domain medical image.

6. The method of claim 5, wherein the second function is $$\varsigma(x; \theta) = 2 \times sigm\left(-\left[\frac{\|x - \hat{x}_1\|^2}{\sigma^2}, \ldots, \frac{\|x - \hat{x}_{p_2}\|^2}{\sigma^2}\right]^T\right),$$

where x denotes the spatial coordinates of the voxels in the source domain medical image, $\sigma$ is a predetermined constant, $p_2$ is a number of hidden nodes in the second layer of the contextual deep network, and $\hat{x}_1, \ldots, \hat{x}_{p_2}$ are augmented variables associated with the hidden nodes of the second layer that are learned in training of the trained contextual deep network.

7. The method of claim 1, wherein the target domain medical image is a segmentation mask image showing a segmented anatomical structure.

8. The method of claim 7, wherein the source image is a computed tomography image, and generating the synthesized target domain medical image using the trained contextual deep network to predict the intensities of the voxels of the target domain medical image based on the intensities and the contextual information of the voxels in the source domain medical image comprises:
generating a segmentation mask image showing a segmented prostate using the trained contextual deep network to predict intensities of voxels of the segmentation mask image based on intensities and spatial locations of voxels in the source computed tomography image.

9. An apparatus for synthesizing a target domain medical image from a source domain medical image, comprising:
means for receiving the source domain medical image; and
means for generating a synthesized target domain medical image using a trained contextual deep network to predict intensities of voxels of the target domain medical image based on intensities and contextual information of voxels in the source domain medical image,
wherein the contextual deep network is a multi-layer network in which hidden nodes of at least one layer of the contextual deep network are modeled as products of intensity responses and contextual response, a response of each hidden node of the at least one layer of the contextual deep network is calculated as a product of a first function of the intensities of the voxels in the source domain medical image and a second function of the contextual information of the voxels in the source domain medical image, and the second function maps the contextual information of the voxels in the source domain medical image to a value of zero or one for each hidden node of the at least one layer of the contextual deep network.

10. The apparatus of claim 9, wherein the contextual information of the voxels in the source domain medical image is spatial locations of the voxels in the source domain medical image.

11. The apparatus of claim 10, wherein the means for generating the synthesized target domain medical image using the trained contextual deep network to predict the intensities of the voxels of the target domain medical image based on the intensities and the contextual information of the voxels in the source domain medical image comprises:
means for extracting intensities of voxels in an image patch of the source domain medical image and spatial coordinates of a center voxel in the image patch of the source domain medical image; and
means for calculating an intensity of a corresponding voxel in the target domain medical image based on the intensities of the voxels in the image patch of the source domain medical image and the spatial coordinates of the center voxel in the image patch of the source domain medical image using the trained contextual deep network, wherein the corresponding voxel in the target domain medical image is a voxel having the same spatial coordinates in the target domain medical image as the center voxel in the image patch of the source domain medical image.

12. The apparatus of claim 9, wherein the at least one layer of comprises a second layer of the contextual deep network.

13. The apparatus of claim 12, wherein the contextual information of the voxels in the source domain medical image is spatial coordinates of the voxels in the source domain medical image.

14. The apparatus of claim 13, wherein the second function is $$\varsigma(x;\theta) = 2 \times sigm\left(-\left[\frac{\|x-\hat{x}_1\|^2}{\sigma^2}, \ldots, \frac{\|x-\hat{x}_{p_2}\|^2}{\sigma^2}\right]^T\right),$$

where x denotes the spatial coordinates of the voxels in the source domain medical image, σ is a predetermined constant, $p_2$ is a number of hidden nodes in the second layer of the contextual deep network, and $\hat{x}_1, \ldots, \hat{x}_{p_2}$ are augmented variables associated with the hidden nodes of the second layer that are learned in training of the trained contextual deep network.

15. The apparatus of claim 9, wherein the target domain medical image is a segmentation mask image showing a segmented anatomical structure.

16. A non-transitory computer readable medium storing computer program instructions for synthesizing a target domain medical image from a source domain medical image, the computer program instructions when executed on a processor cause the processor to perform operations comprising:
receiving the source domain medical image; and
generating a synthesized target domain medical image using a trained contextual deep network to predict intensities of voxels of the target domain medical image based on intensities and contextual information of voxels in the source domain medical image,
wherein the contextual deep network is a multi-layer network in which hidden nodes of at least one layer of the contextual deep network are modeled as products of intensity responses and contextual response, a response of each hidden node of the at least one layer of the contextual deep network is calculated as a product of a first function of the intensities of the voxels in the source domain medical image and a second function of the contextual information of the voxels in the source domain medical image, and the second function maps the contextual information of the voxels in the source domain medical image to a value of zero or one for each hidden nodes of the at least one layer of the contextual deep network.

17. The non-transitory computer readable medium of claim 16, wherein the contextual information of the voxels in the source domain medical image is spatial locations of the voxels in the source domain medical image.

18. The non-transitory computer readable medium of claim 17, wherein generating the synthesized target domain medical image using the trained contextual deep network to predict the intensities of the voxels of the target domain medical image based on the intensities and the contextual information of voxels in the source domain medical image comprises:
for each of a plurality of image patches in the source domain medical image,
extracting intensities of voxels in the image patch and spatial coordinates of a center voxel in the image patch; and
calculating an intensity of a corresponding voxel in the target domain medical image based on the intensities of the voxels in the image patch of the source domain medical image and the spatial coordinates of the center voxel in the image patch of the source domain medical image using the trained contextual deep network, wherein the corresponding voxel in the target domain medical image is a voxel having the same spatial coordinates in the target domain medical image as the center voxel in the image patch of the source domain medical image.

19. The non-transitory computer readable medium of claim 16, wherein the at least one layer of the contextual deep network comprises a second layer of the contextual deep network.

20. The non-transitory computer readable medium of claim 19, wherein the contextual information of the voxels in the source domain medical image is spatial coordinates of the voxels in the source domain medical image.

21. The non-transitory computer readable medium of claim 20, wherein the second function is $$\varsigma(x;\theta) = 2 \times sigm\left(-\left[\frac{\|x-\hat{x}_1\|^2}{\sigma^2}, \ldots, \frac{\|x-\hat{x}_{p_2}\|^2}{\sigma^2}\right]^T\right),$$

where x denotes the spatial coordinates of the voxels in the source domain medical image, σ is a predetermined constant, $p_2$ is a number of hidden nodes in the second layer of the contextual deep network, and $\hat{x}_1, \ldots, \hat{x}_{p_2}$ are augmented variables associated with the hidden nodes of the second layer that are learned in training of the trained contextual deep network.

22. The non-transitory computer readable medium of claim 16, wherein the target domain medical image is a segmentation mask image showing a segmented anatomical structure.

23. The non-transitory computer readable medium of claim 22, wherein the source image is a computed tomography image, and generating the synthesized target domain medical image using the trained contextual deep network to predict the intensities of the voxels of the target domain medical image based on the intensities and the contextual information of the voxels in the source domain medical image comprises:
generating a segmentation mask image showing a segmented prostate using the trained contextual deep network to predict intensities of voxels of the segmentation mask image based on intensities and spatial locations of voxels in the source computed tomography image.

* * * * *